United States Patent [19]

Benkó et al.

[11] Patent Number: 4,511,717
[45] Date of Patent: Apr. 16, 1985

[54] 2-HYDROXYMETHYL-QUINOXALINE-1,4-DIOXIDE DERIVATIVES, A PROCESS FOR PREPARING SAME AND COMPOSITIONS CONTAINING SAME

[75] Inventors: Pál Benkó; Ildikó Rátz née Simonek; László Pallos; Károly Magyar; Jenö Kovács; Erzsébet Mátrai; Janos Gundel, all of Budapest; Albert Balogh, Szentendre, all of Hungary

[73] Assignee: Egyt Gyogyszervegyeszeti Gyar, Budapest, Hungary

[21] Appl. No.: 593,204

[22] PCT Filed: Sep. 11, 1981

[86] PCT No.: PCT/HU81/00038
§ 371 Date: May 7, 1982
§ 102(e) Date: May 7, 1982

[87] PCT Pub. No.: WO82/01001
PCT Pub. Date: Apr. 1, 1982

Related U.S. Application Data

[63] Continuation of Ser. No. 380,741, May 7, 1982, abandoned.

[30] Foreign Application Priority Data

Sep. 12, 1980 [HU] Hungary .............................. 2239/80

[51] Int. Cl.³ .................. C07D 241/52; C07D 403/12; C07D 401/12; A61K 31/495
[52] U.S. Cl. ..................................... 544/353; 544/295
[58] Field of Search ...................... 544/295, 353, 182; 424/249, 250, 251; 426/532

[56] References Cited

U.S. PATENT DOCUMENTS

| | | | |
|---|---|---|---|
| 3,433,871 | 3/1964 | Johnston | 424/250 |
| 3,649,363 | 2/1972 | Kim | 544/353 |
| 3,926,992 | 12/1975 | McFarland | 544/353 |
| 4,100,284 | 7/1978 | Cue | 544/353 |
| 4,221,791 | 9/1980 | Young et al. | 544/353 |

Primary Examiner—Mark L. Berch
Attorney, Agent, or Firm—Karl F. Ross; Herbert Dubno

[57] ABSTRACT

The invention relates to new 2-hydroxymethyl-quinoxaline-1,4-dioxide derivatives of the general formula (I)

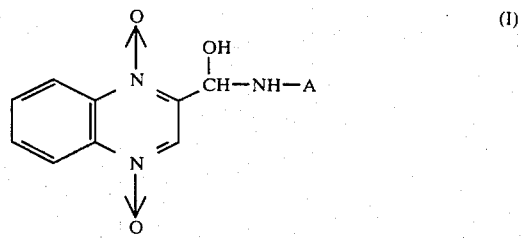

wherein
A represents an amino group, or a group of the general formula —NH—COOR$_1$, wherein R$_1$ stands for a C$_{2-4}$ alkyl group, or a group of the general formula —NH—CX—NH$_2$, wherein
X denotes an oxygen or sulfur atom, or a group of the formula —NH—C(NH)—NH$_2$, or a group of the general formula —NH—R$_2$, wherein R$_2$ represents a C$_{1-6}$ alkyl, a phenyl, a benzyl, a hydroxyl or a hydroxy-(C$_{2-4}$alkyl) group, or a group of the general formula —NH—CO—R$_3$, wherein R$_3$ stands for a C$_{1-20}$ alkyl group or a phenyl group optionally substituted by one, two or three identical or different substituent(s) selected from the group consisting of nitro, hydroxyl, amino, C$_{1-3}$ alkoxy and halogen; a naphtyl group optionally substituted by a hydroxyl group, a phenyl-(C$_{1-3}$ alkyl) group, a pyridyl, a piperidyl, a pyrazinyl, a pyrimidyl, a 1,2,4-triazinyl, a furyl, a nitrofuryl or an α,α-diphenyl-α-hydroxymethyl group.

Due to their antimicrobial and weight-gain increasing effects, the new compounds of the general formula (I) can serve as active ingredients of pharmaceutical or veterinary compositions, particularly fodder concentrates, fodder additives and fodders.

The invention relates also to the preparation of the new compounds of the general formula (I) and the compositions containing same.

4 Claims, No Drawings

2-HYDROXYMETHYL-QUINOXALINE-1,4-DIOXIDE DERIVATIVES, A PROCESS FOR PREPARING SAME AND COMPOSITIONS CONTAINING SAME

CROSS REFERENCE TO RELATED APPLICATION

This application is a continuation of application Ser. No. 380,741, filed May 7, 1982, now abandoned.

This application is a national phase application based upon PCT/HU81/00038 filed Sept. 11, 1981 and based in turn upon Hungarian application No. 2239/80 of Sept. 12, 1980.

FIELD OF THE INVENTION

The invention relates to new 2-hydroxymethyl-quinoxaline-1,4-dioxide derivatives, a process for the preparation thereof and compositions—particularly feed additives, fodder concentrates and animal feeds—containing the same.

BACKGROUND OF THE INVENTION

It is known that certain quinoxaline-1,4-dioxide derivatives possess antimicrobial and weight-gain increasing properties. Such compounds are described in U.S. Pat. No. 3,371,900 and British patent No. 1,479,239.

DESCRIPTION OF THE INVENTION

According to the present invention there are provided new 2-hydroxymethyl-quinoxaline-1,4-dioxide derivatives of the formula (I)

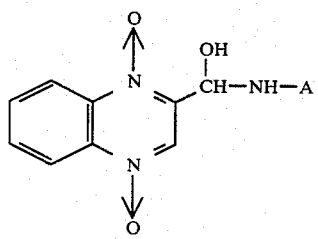

wherein A represents an amino group, or a group of the formula —NH—COOR$_1$, wherein R$_1$ stands for a C$_{2-4}$ alkyl group, or a group of the formula —NH—CX—NH$_2$, wherein X denotes an oxygen or sulfur atom, or a group of the formula —NH—C(=NH)—NH$_2$, or a group of the formula —NH—R$_2$, wherein R$_2$ represents a C$_{1-6}$ alkyl, a phenyl, a benzyl, a hydroxyl or a hydroxy-(C$_{2-4}$ alkyl) group, or a group of the formula —NH—CO—R$_3$, wherein R$_3$ stands for a C$_{1-20}$ alkyl group or a phenyl group optionally substituted by one, two or three identical or different substituents selected from the group consisting of nitro, hydroxyl, amino, C$_{1-3}$ alkoxy and halogen; a naphthyl group optionally substituted by a hydroxyl group, a phenyl-(C$_{1-3}$ alkyl) group, a pyridyl, a piperidyl, a pyrazinyl, a pyrimidyl, a 1,2,4-triazinyl, a furyl, a nitrofuryl or an α,α-diphenyl-α-hydroxymethyl group.

The term "alkyl group" used in the specification and claims covers straight-chained and branched saturated aliphatic hydrocarbyl groups, such as methyl, ethyl, n-propyl, isopropyl, and n-butyl, isobutyl, tert.-butyl. The term "C$_{1-3}$ alkoxy group" relates to straight or branched lower alkylether groups, such as methoxy, ethoxy, n-propoxy or isopropoxy. The term "halogen atom" encompasses all the four halogen atoms, ie. the fluorine, chlorine, bromine and iodine. Preferred representatives of the "hydroxy-(C$_{2-4}$ alkyl) group" are the hydroxyethyl, hydroxypropyl, hydroxyisopropyl and hydroxybutyl groups. The "phenyl-(C$_{1-3}$ alkyl) group" may represent benzyl, α-phenylethyl, β-phenylethyl, β,β-diphenylethyl.

According to a further feature of the invention there is provided a process for the preparation of the compounds of the formula (I), characterized by a. reacting a quinoxaline-1,4-dioxide derivative of the formula (II)

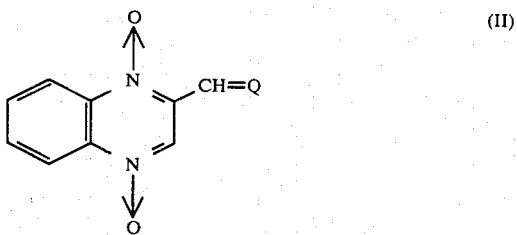

wherein Q represents an oxygen atom or two C$_{1-4}$ alkoxy groups, with a compound of the formula (III)

wherein A has the same meanings as above, or b. to prepare a compound of the formula (I), in which A is a group of the formula —NH—COOR$_1$ or —NH—CO—R$_3$, wherein R$_1$ and R$_3$ have the same meanings as above, reacting 2-(α-hydrazino-α-hydroxymethyl)-quinoxaline-1,4-dioxide of the formula (IV)

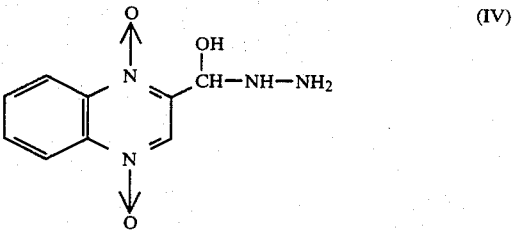

with a carboxylic acid derivative of the formula (V)

wherein R$_4$ has the same meaning as R$_3$, wherein R$_3$ is as defined above, or R$_4$ represents a group of the formula —OR$_1$, wherein R$_1$ is as defined above, and X stands for a leaving group, preferably chlorine.

According to variant a. of the process according to the invention a compound of the formula (II) is reacted with a compound of the formula (III). The reaction is generally performed below 30° C., preferably at about 10° C. to 30° C., in the presence of water or an indifferent organic solvent, such as dimethyl-acetamide, dimethyl-formamide, etc. The reaction is preferably carried out in the presence of a catalyst. As catalyst, preferably mineral acids, such as hydrochloric, sulfuric or phosphoric acid; organic acids, such as p-toluenesulfonic acid; organic bases, such as triethylamine, piperidine, pyrrolidine, morpholine, etc. are used.

When using 2-formyl-quinoxaline-1,4-dioxide-dialkyl-acetal, e.g. dimethyl-acetal as the starting substance of the formula (II), one can also perform the reaction by boiling it in acidic medium for a short time and thereafter reacting the 2-formyl-quinoxaline-1,4-dioxide thus liberated with the compound of the formula (III).

It is also preferred to carry out the reaction without isolating the compound of the formula (III), that is reacting the compound of the formula (II) with the compound of the formula (III) in the same reaction mixture where the latter has been formed.

According to variant b. of the process according to the invention 2-($\alpha$-hydrazino-$\alpha$-hydroxymethyl)-quinoxaline-1,4-dioxide is reacted with a carboxylic acid derivative of the formula (V). Preferred representatives of the compounds of the formula (V) are the carboxylic halides. The reaction is preferably performed in the presence of an acid binding agent. As acid binding agent organic or inorganic bases, e.g. sodium hydrogen carbonate, triethylamine and dimethyl-aniline, can be used. The excess of the reactant of the formula (IV) can also serve as acid binding agent.

When using a carboxylic anhydride as carboxylic acid derivative of the formula (V), acid binding agent is also used to bind the carboxylic acid formed in the reaction.

When using an active ester as carboxylic acid derivative of the formula (V), it is preferred to remove the corresponding alcohol—formed as a by-product—in the course of the reaction.

The starting substances of the formula (V) are known compounds [Zs. Obscs. Him., 25, 161 (1955)].

The reactants of the formula (III) and (V) are similarly known [J. Zabiczky, The Chemistry of Amides, Ch. 10, 515, Interscience Publ., 1970.]

The new compounds of the formula (I) can serve as starting substances for the preparation of known derivatives possessing weight-gain increasing effects. Furthermore, due to their antimicrobial and weight-gain increasing properties, they can be used in therapy or in animal husbandry. These compounds are active against a wide range of gram-positive or gram-negative bacteria, e.g. against the following microorganisms: Enterobacteriaceae, such as *Escherichia coli*, Pseudomonadaceae, such as *Pseudomonas aeruginosa*, Micrococcaceae, such as *Staphylococcus aureus*.

The excellent and wide-spread antimicrobial effect of the new compounds of the formula (I) enables them to be used either locally or in a systemic manner for the prophylaxis or treatment of various bacterial infections.

According to a further feature of the invention there are provided compositions for use in therapy or in animal husbandry containing as active ingredient an effective amount of a compound of the formula (I) wherein A is as defined above, optionally along with a known ingredient, in admixture with suitable inert solid or liquid carriers or diluents.

These compositions can be presented in forms generally used in therapy or in veterinary practice, such as tablets, coated tablets, injections, boluses, etc., and may contain the usual inert carriers, diluents and additives. The said compositions can be prepared by methods well known in the pharmaceutical industry.

The compositions of the present invention may be particularly fodder additives, fodder concentrates and fodders containing as active ingredient an effective amount of a compound of the formula (I), wherein A is as defined above, optionally along with a known ingredient, in admixture with suitable edible said solid or liquid carriers or diluents and additives.

According to a further feature of the invention there is provided a process for the preparation of pharmaceutical or veterinary compositions, particularly fodder additives, fodder concentrates and fodders, which comprises admixing a compound of the formula (I), wherein A has the same meanings as above, and optionally a further known ingredient, with a suitable edible solid or liquid carrier or diluent and additive generally used in the production of such compositions.

As carrier or diluent any substance of vegetable or animal origin applicable in the feeding of animals or serving as fodder can be used. For this purpose e.g. wheat, rice, maize, soybean, alfalfa, barley, oats, rye can be used in appropriate forms (grits, groats, meal, bran, etc.), furthermore fish meal, meat meal, bone meal or mixtures thereof can be used as well. One may advantageously use a fiber-free green plant fodder concentrate with high protein content (e.g. VEPEX ®).

As additives e.g. silicic acid, wetting agents, antioxidants, starch, dicalcium phosphate, calcium carbonate or sorbic acid, can be used. As wetting agent e.g. nontoxic oils, preferably soybean oil, maize oil or mineral oil can be applied. Various alkylene glycols can also be used as wetting agent. The starch used may be wheat, maize or potato starch.

The fodder additives and concentrates may contain usual vitamins (e.g. vitamin A, $B_1$, $B_2$, $B_3$, $B_6$, $B_{12}$, E, K) and also trace elements (e.g. Mn, Fe, Zn, Cu, I).

The active ingredient content of the compositions according to the invention may vary within a wide range. The fodder additives and concentrates may contain about 5–80% by weight, preferably about 10–50% by weight of the active ingredient of the formula (I). The active ingredient content of the animal fodders ready for use may be about 1–400 ppm, preferably about 10–100 ppm.

The fodder concentrates and additives are diluted with suitable fodder components or are incorporated into suitable animal feeds to provide animal feeds ready for use. The new compounds of the general formula (I) can also be used by admixing them with the drinking-water.

The fodders according to the present invention can be used for the increase of weight-gain and improvement of feed utilization of various domestic animals, such as pigs, lambs, cattle and poultry, particularly pigs.

SPECIFIC EXAMPLES

Further details of the present invention are to be found in the following Examples without limiting the scope of the invention to the Examples.

EXAMPLE 1

Preparation of 2-[$\alpha$-(p-hydroxybenzoyl-hydrazino)-$\alpha$-hydroxy-methyl]-quinoline-1,4-dioxide 9.5 g (0.05 moles) of 2-formyl-quinoxaline-1,4-dioxide and 7.6 g (0.05 moles) of p-hydroxybenzoic hydrazide are allowed to react in 250 ml of water, in the presence of 2 drops of piperidine at 25° C. for 3 hours. The separated product is filtered off and washed with water. 16.7 g (97.6%) of desired compound are obtained.

M.p.: 305°–306° C.

EXAMPLE 2

Preparation of 2-[$\alpha$-(p-chlorobenzoyl-hydrazino)-$\alpha$-hydroxy-methyl]-quinoxaline-1,4-dioxide 9.5 g (0.05 moles) of 2-formyl-quinoxaline-1,4-dioxide and 8.5 g (0.05 moles) of p-chlorobenzoic hydrazide are allowed to react in 250 ml of dimethylformamide, in the presence of 2 drops of piperidine at 10° C. for an hour, then the reaction mixture is warmed up to 30° C. and allowed to react further for 2 hours. The separated product is filtered off and washed with water. 17.1 g (95%) of desired compound are obtained.

M.p.: 258°–259° C.

EXAMPLE 3

Preparation of 2-(α-hydrazino-α-hydroxymethyl)-quinoxaline-1,4-dioxide 9.5 g (0.05 moles) of 2-formyl-quinoxaline-1,4-dioxide and 1.6 g (0.05 moles) of hydrazine are allowed to react in 50 ml of dimethylformamide at 10° C. for 3 hours. The separated product is filtered off. 8.75 g (79%) of desired compound are obtained.

M.p.: 217°–218° C.

The compounds listed in the following Table are prepared by the methods of the previous Examples:

| Example No. | A | Solvent | Method (No. of) the Example) | Catalyst | Temperature (°C.) | M.p. (°C.) | Yield (%) |
|---|---|---|---|---|---|---|---|
| 4. | laurinoyl-amino | water | 1. | HCl | 25 | 200 | 84 |
| 5. | 3-nitrobenzoyl-amino | water | 1. | piperidine | 25 | 274–75 | 89 |
| 6. | 4-chlorobenzoyl-amino | water | 1. | piperidine | 30 | 257 | 88 |
| 7. | 3,5-dimethoxy-benzoyl-amino | acetonitril | 2. | piperidine | 25 | 230–31 | 95 |
| 8. | phenyl-acetyl-amino | dimethyl-formamide | 2. | piperidine | 10 | 242 | 90 |
| 9. | 2-nitrobenzoyl-amino | isopropanol | 1. | piperidine | 10 | 250 | 93 |
| 10. | isonicotinoyl-amino | isopropanol | 1. | piperidine | 10 | 241 | 85 |
| 11. | isonicotinoyl-amino | acetonitrile | 3. | — | 20 | 241 | 88 |
| 12. | heptanoyl-amino | water | 1. | piperidine | 10 | 212–13 | 86 |
| 13. | 3,4,5-trimethoxy-benzoly-amino | isopropanol | 1. | piperidine | 10 | 247–48 | 87 |
| 14. | 5-nitrofuran-2-carbonyl-amino | water | 1. | piperidine | 10 | 275 | 92 |

What we claim is:

1. A compound of the formula

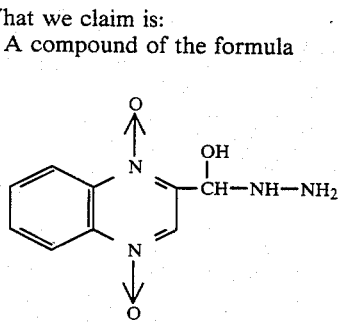

2. A compound of the formula

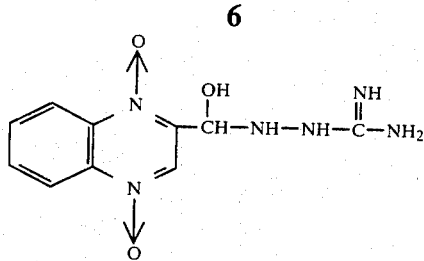

3. A compound of the formula

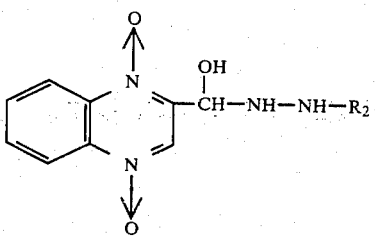

wherein R₂ is $C_1-C_6$ alkyl, phenyl, benzyl, hydroxy, or hydroxy-$(C_2-C_4)$-alkyl.

4. A compound of the formula

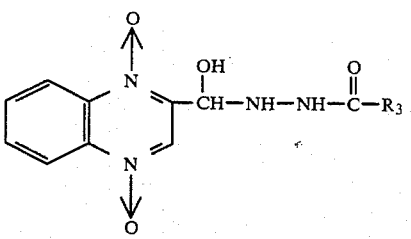

wherein R₃ is $C_1-C_{20}$ alkyl, phenyl unsubstituted or substituted by one, two or three identical or different substituents selected from the group consisting of nitro, hydroxy, amino, $C_1-C_3$ alkoxy, and halogen, or R₃ is naphthyl, hydroxy-naphthyl, phenyl-$(C_1-C_3)$-alkyl, pyridyl, piperidyl, pyrazinyl, pyrimidyl, 1,2,4-triazinyl, furyl, nitro-furyl, or alpha, alpha-diphenyl-alpha-hydroxymethyl.

* * * * *